United States Patent [19]

Renga

[11] 4,375,549
[45] Mar. 1, 1983

[54] PROCESS FOR MAKING SILYL ETHERS

[75] Inventor: James M. Renga, Midland, Mich.

[73] Assignee: The Dow Chemical Company, Midland, Mich.

[21] Appl. No.: 355,636

[22] Filed: Mar. 8, 1982

Related U.S. Application Data

[63] Continuation-in-part of Ser. No. 278,786, Jun. 29, 1981, abandoned.

[51] Int. Cl.$^3$ ............................ C07F 7/04; C07F 7/18
[52] U.S. Cl. ................................... 556/470; 546/14; 548/110; 549/4; 549/479; 548/406
[58] Field of Search ..................... 556/470; 546/14; 548/110; 549/4, 429; 260/326.61

[56] References Cited

U.S. PATENT DOCUMENTS 3,472,888 10/1969 Bazouin et al. ..................... 556/470
3,856,843 12/1974 Nagai et al. ..................... 556/470 X

FOREIGN PATENT DOCUMENTS 1227022 10/1966 Fed. Rep. of Germany ...... 556/470

OTHER PUBLICATIONS

Hans R. Kricheldorf, Angew. Chem. Int. Ed. (Engl.) 18, 689–690 (1970).

*Primary Examiner*—Paul F. Shaver
*Attorney, Agent, or Firm*—Douglas N. Deline

[57] ABSTRACT

Organic silyl ethers are prepared by contacting an acyclic carbonate ester with an organic silyl halide in the presence of an initiator compound at a temperature from about 50° C. to about 250° C.

8 Claims, No Drawings

PROCESS FOR MAKING SILYL ETHERS

CROSS-REFERENCE TO RELATED APPLICATION

This is a continuation-in-part of my copending application Ser. No. 278,786, filed June 29, 1981, now abandoned.

BACKGROUND OF THE INVENTION

This invention concerns a new chemical process for making organic silanes having alkoxy or aryloxy substituents, also named as organic silyl ethers. Such ethers have various uses. Monomeric ethers of this type are valuable functional fluids while polymeric ethers preparable by this process are useful moldable plastics.

Silyl ethers have been made in the past by reacting an organic silyl halide with an alcohol or phenol in the presence of an acid acceptor. Other silyl reagents such as hexaalkyldisiloxanes, dialkylaminodialkylsilanes, and organocyclosilazanes have been used in this kind of reaction. Organic halides have been reacted with alkoxysilyl halides in the presence of metallic sodium to make the corresponding silyl ethers. These processes have various disadvantages such as high reaction temperatures, strongly basic or acidic reaction mixtures, and the production of salt by-products that have to be separated from the silyl ether product.

The reaction of certain mixed aryl alkyl carbonates with an organic halide to produce an aromatic ether is described in my copending application entitled "Process for Making Aromatic Ethers", Ser. No. 187,688, filed Sept. 16, 1980. It is also known that a trimethylsilyl halide reacts with a cyclic alkylene carbonate to make a halogenated silyl ether, see Kricheldorf, *Angew. Chem. Int. Ed.* (Engl.) 18, 689 (1979).

SUMMARY OF THE INVENTION

It has now been found that a lower alkyl carbonate of the formula $R(OCO_2R')_m$ reacts with a reactive aryl, alkyl, or heterocyclic silyl halide of the formula $R''_{4-n}SiX_n$ in the presence of an initiator compound at about 50° C.–250° C. to produce a high yield of the corresponding organic silyl ether with elimination of the relatively volatile lower alkyl halide and $CO_2$ as coproducts of the reaction.

In the above formulas, m and n are each an integer from one to three, m representing the valence of R. R is an aliphatic, cycloaliphatic, heterocyclic, or any carbocyclic or heterocyclic aromatic group, unsubstituted or substituted with one or more groups unreactive in the reaction, R' is a lower alkyl or halogenated lower alkyl group, R'' is hydrogen or an aliphatic, cycloaliphatic, aromatic, or heterocyclic group, saturated or unsaturated, unsubstituted or substituted with one or more groups unreactive in the reaction, and X is Cl, Br, or I.

DETAILED DESCRIPTION OF THE INVENTION

Depending upon the values of m and n in the above formulas, the reaction produces a monoether or polyether as shown in the following equation:

$$nR(OCO_2R')_m + mR''_{4-n}SiX_n \rightarrow (R''_{4-n}Si)_mO_{mn}R_n + mnR'X + mnCO_2.$$

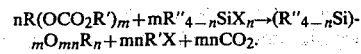 is an empirical formula representing different kinds of ethers. When, as preferred, both m and n are one or one of m and n is one and the other is two, a monoether or a diether is the ether product. When both m and n are greater than one, preferably two, a polymeric polyether structure is produced and the empirical formula represents a unit in the molecular structure of the polymeric polyether.

In the above equation and formulas, a monovalent R can be alkyl, cycloalkyl, phenyl, naphthyl, biphenylyl, pyridyl, furyl, quinolyl, benzofuryl, pyridazyl, indolyl, benzothiazolyl, or the like, unsubstituted or substituted with up to about three unreactive groups. Such substituents include lower alkyl, lower alkoxy, halo, nitro, ester groups, trifluoromethyl, aralkyl, and phenoxy. When m is greater than one, R represents the divalent or trivalent equivalents of the above, e.g., alkylene, cycloalkylene, phenylene, naphthylylene, alkylidenediphenylene, alkylenetriphenylene, oxydiphenylene, and the like, also substituted or unsubstituted as described. An aromatic or cycloaliphatic R preferably represents monocyclic groups such as cyclohexyl, cyclohexylmethyl, phenyl, phenylene, alkylidenediphenylene, and pyridyl.

The groups represented by R'' are hydrogen or monovalent, hydrocarbon and heterocyclic groups which may have unreactive substituents. Thus, besides hydrogen, R'' can be an aliphatic, cycloaliphatic, aromatic, or heterocyclic group such as alkyl of about 1–20 carbon atoms; an olefinic group of about 2–20 carbon atoms such as vinyl allyl, butenyl, octenyl, hexadecenyl, pentadienyl, and octadienyl; an alicyclic group such as cyclopentyl and cyclohexyl; carbocyclic aryl and aralkyl groups such as phenyl, naphthyl, and benzyl; or a heterocyclic group such as pyridyl, furyl, quinolyl, indolyl, benzothiazolyl, benzofuryl, and the like.

In the reaction generally, R' is preferably a methyl group so that the by-product R'X is vaporized readily and leaves the reaction mixture substantially as the $CO_2$ comes off, thereby minimizing the undesirable side reaction of R'X with the unreacted starting carbonate.

The reactive halogen X can be chlorine, bromine or iodine and is preferably chlorine. It is necessary that X be reactive in the process under the conditions described and such reactivity may be conferred by either the configuration of R'' or by one or more activating substituents on R''. Thus, a normally unreactive chlorine atom on a benzene ring may be rendered reactive by one or more other substituents such as the nitro group.

The group R' in the above equation can be methyl, ethyl, propyl, butyl, or iodo-, bromo-, chloro- or fluoro-substituted derivatives thereof, but is most preferably a methyl group. The reaction proceeds with elimination of $CO_2$ and the volatile halide product R'X. Consequently, when R'X is the highly volatile methyl chloride, the reaction is particularly accelerated and separation of the ether product is also thereby facilitated.

Although the process can be operated at any temperature in the broad range of about 50° C.–250° C. as previously stated, it is preferably carried out at about 100° C.–175° C. for most convenient operation conditions and reaction time. The reaction time can vary from about 0.1 hour to about 10 hours depending upon the reaction conditions.

A reaction solvent is usually not required or desirable, but use of a solvent may be advantageous under some conditions, e.g., when low boiling reactants or solid reaction products are involved. Polar solvents appear to increase the rate of reaction. Relatively high boiling inert solvents such as N,N-dimethylformamide, sulfolane, glycol diethers, and substituted aromatics such as anisole, o-dichlorobenzene, alkylated pyridines, and the like are preferred.

Initiator compounds that are suitably employed in the process include those compounds that act as catalysts in the process and also those compounds that themselves may not possess catalytic properties but are capable of forming catalysts in situ. Catalysts include acids, bases and salts. Examples of acid catalysts include mineral acids, organic acids and solid acids such as Lewis acids, and acidic ion-exchange materials such as natural or artificial zeolites or organic ion-exchange resins. Basic catalysts include both organic and inorganic bases and basic ion-exchange materials. Salts include metal salts of acids such as metal halides, sulfate or bicarbonates and quaternary salts such as ammonium, sulfonium, sulfoxonium or phosphonium salts. Other suitable initiators are those compounds capable of forming in situ one or more of the above catalysts. Examples of the latter include amine or phosphine compounds capable of reaction with further components of the reaction mixture, e.g., organic halogen compounds, to form ammonium or phosphonium salts.

More particularly, acid catalysts include sulfuric acid, hydrochloric acid, toluene sulfonic acid, potassium bisulfate, zinc chloride, aluminum chloride, and acid-exchanged resins of chlorinated (poly)styrene cross-linked with divinylbenzene or similar cross-linking substance. Basic compounds include amines such as pyridine or triethylamine, and alkali metal hydroxides or carbonates. Salts include inorganic sulfate, nitrate, phosphate or halide salts, or organic formate, acetate, benzoate, phenate or bisphenate salts of alkali metals, alkaline earth metals, metals of groups Ib, IIb and VIII of the Periodic Table and ammonium, sulfonium, sulfoxonium or phosphonium quaternary ions. The latter class of ammonium or phosphonium quaternary ions are additionally described as follows.

Preferably, these salts have the general formula $(R''')_4AY$ where each $R'''$ is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The $R'''$ groups may be alkyl, aryl, alkaryl, aralkyl, or cycloalkyl. Also, two $R'''$ groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above.

Also, amine and phosphine salts such as tributylamine hydrochloride which are a form of quaternary salt will catalyze the reaction although these are generally less desirable in the reaction mixture. Additionally, it is possible to form the quaternary salt in situ. For example, when a nitrogen-containing solvent such as N,N-dimethylformamide or N,N-dimethylacetamide is employed in the process, the small amount of quaternary salt formed by interaction of the amide nitrogen atom with the halide reactant (or alkyl halide product) is sufficient to catalyze the reaction. The same is true if a small amount of amine or phosphine compound is added to the reaction mixture to form such quaternary salt.

Although any significant amount of the previously identified initiator compound will catalyze the reaction to some extent, for practical reasons in batch operations, it is preferred to use a catalytic amount, e.g., about 0.1–10 mole percent of the initiator based on the carbonate. Where it is necessary to solubilize the catalysts, particularly the salt catalysts, a solubilizing agent such as a chelating agent, e.g., a crown ether may additionally be employed according to known techniques in the art. More initiator can be used but the excess confers little added advantage and may in fact be disadvantageous. The preferred initiators are ammonium or phosphonium salts that allow the reaction process to be conducted under relatively neutral reaction conditions.

In a mode of the invention particularly adapted to continuous operation, one or more R groups may be pendant methylene groups from a resin matrix so that the quaternary salt is a salt form of a strong base anion-exchange resin such as DOWEX ® 21K, DOWEX ® 11, DOWEX ® MWA-1, or other such commercially available ion-exchange resins or the phosphonium equivalents of such quaternary ammonium-substituted resins. In such a continuous operation of the process, the mixed reactants are passed at an appropriate flow rate through a bed of the strong base anion resin maintained at a suitable temperature within the limits previously defined.

Batchwise operation of the process involves simply combining the reactants and catalyst and heating until the evolution of carbon dioxide and alkyl halide has ceased.

The process is ordinarily carried out at atmospheric pressure but it may be carried out at somewhat reduced pressure to hasten the removal by distillation of the volatile alkyl halide product. Passage of a stream of nitrogen or other inert gas through or over the reaction mixture may also be beneficial in this respect for some mixtures.

This process provides the advantages of a neutral reaction mixture, moderate temperature, and ready separation of the ether product as well as the alkyl halide coproduct. The volatile reaction products are carbon dioxide which can simply be vented and the alkyl halide which can be recovered by condensation or adsorption. The residue in the reaction vessel is primarily the desired ether together with the small amount of the initiator compound and, in some cases, a minor amount of the alkyl ether produced by the decomposition of the carbonate reactant. The desired ether product is readily recovered and purified by conventional means such as distillation or recrystallization depending on its physical properties.

The monomeric organic silyl ethers are useful functional fluids such as heat exchange liquids, hydraulic fluids, and dielectric liquids, particularly valuable because of their chemical unreactivity and relatively low freezing points. The polymeric ethers are readily moldable solid plastics.

The alkyl carbonate starting material can be made by any of several known methods for making these mixed esters. A common preparatory method is the reaction of an alcohol, a phenol or a corresponding hydroxyl substituted heterocyclic compound such as a pyridinol with an alkyl chloroformate under basic conditions. Asymmetric carbonates can also be made by the acid or base catalyzed transesterification reaction of an alcohol or phenol with a symmetrical carbonate ester, for example, the reaction of phenol with dimethyl carbonate to make methyl phenyl carbonate and the corresponding reaction of a pyridinol to make the methyl pyridyl carbonate.

EXAMPLE 1

A mixture of 3.8 g (0.025 g mole) of methyl phenyl carbonate, 3.83 g (0.025 g mole) of trimethylbromosilane, and 0.09 g of tetra-n-butyl phosphonium bromide in 15 ml of sulfolane was heated at 120° C. in a reaction flask equipped with a reflux condenser. After 16 hours of heating, the reflux condenser was replaced by a distillation head and 2.7 g (65 percent yield) of phenoxytrimethylsilane was distilled at reduced pressure from the reaction mixture at a head temperature of 71° C.–72° C./18 mm Hg.

EXAMPLE 2

In the apparatus of Example 1, a mixture of 3.8 g (0.025 g mole) of methyl phenyl carbonate, 1.94 g (0.015 g mole) of dimethyldichlorosilane, and 0.1 g of tetra-n-butyl phosphonium bromide was heated at 140° C. After one hour, little apparent reaction had taken place so 0.1 g of tetra-n-butyl phosphonium formate was added to the reaction mixture. Rapid evolution of $CO_2$ resulted and after one hour of heating this mixture at 140° C., more than 96 percent of the methyl phenyl carbonate had been converted as indicated by nuclear magnetic resonance spectroscopic analysis of the reaction mixture. Distillation of the reaction mixture under reduced pressure produced 2.7 g (89 percent yield) of dimethyldiphenoxysilane, b.p. 100° C.–101° C./0.3 mm Hg.

EXAMPLE 3

In the manner described above, a mixture of 3.24 g (0.036 g mole) of dimethyl carbonate, 3.96 g (0.015 g mole) of 96 percent diphenyldichlorosilane, and 0.5 g of tetra-n-butyl phosphonium bromide in 15 ml of sulfolane was heated at 150° C. for 16 hours. The reaction mixture was then added to 200 ml of icewater and the organic portion was extracted with two 25-ml portions of hexane. After the extract was dried over anhydrous $MgSO_4$, the solvent was distilled off and the residual material was distilled under reduced pressure to obtain 2.87 g (78 percent yield) of diphenyldimethoxysilane, b.p. 93° C.–94° C./0.1 mm Hg.

EXAMPLES 4–7

Using the procedure of Example 2, molar equivalent proportions of methyl phenyl carbonate and a phenyl () silyl chloride were heated at 150° C. in the presence of 1.0 mole percent of tetra-n-butyl phosphonium bromide based on the carbonate. In each case, essentially all of the carbonate reacted to produce about a 95 percent yield of the expected substituted silane. These results are summarized in the table.

| Example No. | Silyl Chloride Reactant | Time, hrs. | Product |
|---|---|---|---|
| 4 | φ(CH$_3$)SiCl$_2$ | 0.33 | φ(φO)$_2$SiCH$_3$ b.p. 142–3° C./0.3 mm Hg |
| 5 | φ$_2$SiCl$_2$ | 1.0 | (φO)$_2$Siφ$_2$ b.p. 180–2° C./1 mm Hg |
| 6 | φSiCl$_3$ | 2.0 | (φO)$_3$Siφ b.p. 180–3° C./0.1 mm Hg |
| 7 | φ$_3$SiCl | 1.0 | φOSiφ$_3$ b.p. 170–180° C./0.2 mm Hg |

EXAMPLE 8

A mixture of 6.887 g (0.02 mole) of bisphenol A bis(methyl carbonate), 2.84 g (0.022 mole) of dimethyldichlorosilane, and 0.14 g of tetra-n-butyl phosphonium bromide in 25 ml of o-dichlorobenzene was heated at 180° C. in a resin pot for 2 hours with vigorous stirring. The liquid reaction mixture was then put in a vacuum evaporator and the volatile materials were removed by heating at 150° C. under reduced pressure for 18 hours. The residue was a brittle yellow polymeric solid melting at 65° C.–70° C. wherein the linear polymer molecules consisted essentially of alternating dimethylsilyl and isopropylidenediphenoxy moieties. This polymeric product had an inherent viscosity $n_{inh}$ at 25° C. in dioxane of 0.13 dl/g. Its average molecular weight was estimated at about 7000 by nuclear magnetic resonance spectroscopy.

EXAMPLE 9

In the manner described in Examples 1–7, diphenyldichlorosilane was reacted with about two moles of methyl 3,5,6-trichloro-2-pyridyl carbonate in the presence of tetrabutylammonium chloride to produce a good yield of diphenyl bis(3,5,6-trichloro-2-pyridyloxy)silane, a crystalline solid.

EXAMPLE 10

As generally described in Example 8, approximately equal molar proportions of (CH$_3$)$_2$SiCl$_2$ and 1,4-cyclohexylenedimethylene bis(methyl carbonate) were reacted to produce a near quantitative yield of a linear polymeric polyether of which the molecular structure consisted essentially of alternating 1,4-cyclohexylenedimethylene and dimethylsiloxane moieties.

By the general procedure described in the foregoing examples, other aliphatic and aromatic silyl halides are reacted with various lower alkyl carbonates to produce the corresponding organic silyl ethers. In this way, methyl octyl carbonate is reacted with dimethyldichlorosilane to make bis(octyloxy)dimethylsilane, phenyl carbonate is reacted with tributyl chlorosilane to produce tributyl phenoxysilane, and cyclohexyl methyl carbonate is reacted with ditolyl dichlorosilane to make dicyclohexyloxy ditolylsilane.

EXAMPLE 11

A mixture of 5.61 g (0.03 mole) of bis(2-chloroethyl)carbonate, 3.0 g (0.015 mole) of 96 percent dichloromethylphenyl silane, and 0.1 g (0.0003 mole) of tetra-n-butyl phosphonium bromide was heated to 175° C. in a reaction flask equipped with a distillation head. After 10 hours, 2.9 g (98 percent yield) of 1,2-dichloroethane had collected. Further distillation gave 3.85 g (92 percent yield) of bis(2-chloroethoxy)methylphenyl silane, b.p. 97° C.–98° C./0.2 mm Hg.

EXAMPLE 12

The reaction procedure of Example 11 was substantially repeated employing 6.03 g (0.03 mole) of 2-chloroethyl 1-chloro-2-propyl carbonate. The product, 3.35 g (73 percent yield) comprised bis(1-chloro-2- propoxy)methylphenyl silane, b.p. 109° C.-110° C./0.2 mm Hg.

EXAMPLE 13

The procedure of Example 11 was substantially repeated employing 4.58 g (0.03 mole) of 2-chloroethyl ethyl carbonate. 2.8 g (67 Percent yield) of bis(2-chloroethoxy)methylphenyl silane was recovered, b.p. 97° C.-98° C./0.2 mm Hg.

I claim:

1. A process for making an organic silyl ether of the empirical formula $(R''_{4-n}Si)_m O_{mn} R_n$ which comprises contacting a carbonate of the formula $R(OCO_2R')_m$ with an organic silyl halide of the formula $R''_{4-n}SiX_n$ in the presence of a catalytic amount of an initiator compound at about 50° C.-250° C. and separating said silyl ether from the resulting reaction mixture, wherein R is an aliphatic, cycloaliphatic, heterocyclic, or aromatic group having a valence of m, R' is a lower alkyl or halogenated lower alkyl group, R" is hydrogen or an aliphatic, cycloaliphatic, aromatic, or heterocyclic monovalent group, m and n each represent an integer from one to three, and X is Cl, Br, or I.

2. The process of claim 1 wherein m and n are both one.

3. The process of claim 2 wherein R' is a methyl group.

4. The process of claim 3 wherein X is Cl.

5. The process of claim 2 wherein the temperature is about 100° C.-175° C.

6. The process of claim 1 wherein m and n are both two and the organic silyl ether product is a polymeric polyether.

7. The process of claim 6 wherein R is an isopropylidenediphenylene group and R" represents a methyl group.

8. The process of claim 1 wherein the initiator compound is an acid selected from the group consisting of mineral acids, organic acids, Lewis acids and acidic ion-exchange materials; a base selected from amines, alkali metal hydroxides, and alkali metal carbonates, or a salt selected from the group consisting of sulfate, nitrate, phosphate, halide, formate, acetate, benzoate, phenate and bisphenate salts of alkali metals, alkaline earth metals, metals of Groups Ib, IIb or VIII of the Periodic Table and ammonium, sulfonium, sulfoxonium or phosphonium quaternary ions.

* * * * *